United States Patent [19]
Jansen et al.

[11] Patent Number: 5,869,457
[45] Date of Patent: Feb. 9, 1999

[54] MODIFIED PROTEINS AND THEIR USE FOR CONTROLLING VIRAL INFECTIONS

[75] Inventors: Robert Walter Jansen, Losser; Dirk Klaas Fokke Meijer; Grietje Molema, both of Groningen; Erik Desire Alice De Clercq, Lovenjoel; Rudi Wilfried Jan Pauwels, Weerde; Dominique Schols, Herent, all of Netherlands

[73] Assignee: Rijksuniversiteit Te Groningen, Netherlands

[21] Appl. No.: 923,232

[22] Filed: Sep. 4, 1997

Related U.S. Application Data

[63] Continuation of Ser. No. 443,907, May 17, 1995, abandoned, which is a continuation-in-part of Ser. No. 119,042, Nov. 4, 1993, abandoned.

[30] Foreign Application Priority Data

Nov. 3, 1991 [NL] Netherlands ............................ 9100434

[51] Int. Cl.$^6$ ............................ A61K 38/04; A61K 38/16
[52] U.S. Cl. ................................. 514/21; 514/8; 530/362; 530/363; 530/395; 530/402; 530/409; 530/410
[58] Field of Search ........................... 514/8, 21; 530/362, 530/363, 395, 402, 409, 410

[56] References Cited

U.S. PATENT DOCUMENTS

| | | | |
|---|---|---|---|
| 3,558,459 | 1/1971 | Gransliand et al. ..................... | 204/180 |
| 4,160,825 | 7/1979 | Sikes ......................................... | 424/85 |
| 4,165,370 | 8/1979 | Coval ....................................... | 424/85 |
| 4,356,173 | 10/1982 | Miura et al. ............................. | 424/101 |
| 5,322,678 | 6/1994 | Morgan, Jr. et al. ................... | 424/1.53 |

FOREIGN PATENT DOCUMENTS

| | | |
|---|---|---|
| 0406416 | 1/1991 | European Pat. Off. . |
| 2625902 | 7/1989 | France . |

OTHER PUBLICATIONS

Hirsch, Am. J. of Med., vol. 85 (suppl. 2A), pp. 182–185, 1988.

Jansen et al., Pharm. Res., vol. 10 (11), pp. 1611–1614, 1993.

Osband et al., Immunol. Today, vol. 11 (6), pp. 193–195, 1990.

Fauci, Science, vol. 239, pp. 617–622, 1988.

Stein et al., Clin. Inf. Diseases, vol. 17, pp. 749–771, 1993.

Fox, Bio/Technology, vol. 12, p. 128, 1994.

Fahey et al., Clin. Exp. Immunol., vol. 88, pp. 1–5, 1992.

Harris et al., "Protein Purification Methods", IRL Press, pp. 57–64, 1989.

*Primary Examiner*—Chhaya D. Sayala
*Attorney, Agent, or Firm*—Bachman & LaPointe, P.C.

[57] ABSTRACT

The invention relates to pharmaceutical preparations which are suitable for treating viral infections, including influenza and immunodeficiency diseases and which can also be used in vitro, to inhibit fusion of virus-infected cells with non-infected cells, which preparations contain modified proteins or polypeptides as active substance or substance contributing to the action or as carrier for other substances, which are also active, which modified proteins or polypeptides have acquired an additional net negative charge by derivatisation of their amino groups and/or other basic functional groups with aconitic acid which prevents protonation of basic amino acids and/or other basic functional groups or replaces basic amino acids and/or other basic functional groups by one or more functional groups having a negative charge, and to modified proteins and polypeptides themselves and their preparation and use.

32 Claims, No Drawings

MODIFIED PROTEINS AND THEIR USE FOR CONTROLLING VIRAL INFECTIONS

CROSS-REFERENCE TO RELATED APPLICATION

This is a continuation of application Ser. No. 08/443,907 filed on May 5, 1995, abandoned, which application is a Continuation-In-Part of U.S. patent application Ser. No. 08/119,042, filed Nov. 4, 1993 abandoned.

BACKGROUND OF THE INVENTION

The invention relates to pharmaceutical preparations which are suitable for treating or curing viral infections, including influenza and immunodeficiency diseases such as retrovirus infections, including AIDS and AIDS-related diseases, and which can also be used to inhibit fusion of virus-infected cells with non-infected cells, which preparations contain modified proteins or polypeptides as active substance or substance contributing to the action or as carrier for other substances, which are also active.

The use of glycoproteins as cell-specific carriers for 3'-azido-3'-desoxythymidine (AZT) is disclosed in the publication by Molema, G., Jansen, R. W. Pauwels, R., De Clerg, E., and Meijer, D. K. F. in Biochem. Pharmacol. part 40, No. 12, pp. 2603–2610 (1990). To date AZT is the only registered agent for the treatment of AIDS. AZT blocks the synthesis of viral DNA in the infected cells. Although AIDS is not cured, the agent prolongs life expectancy. Unfortunately, AZT also attacks healthy cells and therefore gives rise to a large number of undesirable side effects. These side effects arise in particular in tissues where a large amount of DNA is produced, for example in bone marrow. According to the abovementioned publication, it is proposed to direct AZT to target cells with the aid of a carrier molecule. According to the abovementioned publication, conjugates of albumin (HSA) and sugars, for example mannose, fucose, galactose and glucose, are prepared and tested for their anti-HIV activity in combination with AZTMP (AZT phosphorylated to the monophosphate form). It is presumed that the carrier molecule releases the active substance once the conjugate of glycoprotein and active substance has been absorbed by the target cell.

The use of sulphated phenyl polymers in preparations for the treatment of retrovirus infections is disclosed in Netherlands Patent Application 8900442. Sulphated phenyl polymers mentioned in this publication are sulphated polyphenyl alcohols, sulphated copolymers of (meth)acrylic acid and phenyl alcohol and pharmaceutically acceptable salts thereof. These active substances reduce the cytopathogenicity of HIV-1 in MT-4 cells and the antigen expression of HIV-1 in CEM cells. They are also active against the replication of HIV-2. In addition, the formation of giant cells (multinuclear syncytium cells), generated by HIV-1, and the adsorption of HIV fragments on CD-4 positive cells are inhibited.

SUMMARY OF THE INVENTION

The invention relates to pharmaceutical preparations which are suitable for treating or curing viral infections and immuno-deficiency diseases such as retrovirus infections, including AIDS and AIDS-related diseases, and which can also be used to inhibit fusion of virus-infected cells with non-infected cells, which preparations contain modified proteins or polypeptides as active substance or substance contributing to the action or as carrier for other substances, which are also active, which modified proteins or polypeptides have acquired an additional net negative charge by derivatisation of their amino groups and/or other basic functional groups with a reagent which prevents protonation of basic amino acids and/or other basic functional groups or replaces said basic amino acids and/or other basic functional groups by one or more functional groups having a negative charge, the prolongation of the retention time of the protein or polypeptide derivative compared with that of the protein or polypeptide not converted to a derivative being at least 9 minutes, the retention time being determined by means of FPLC on an anion exchange column.

The present invention is based on the finding that a correlation exists between the negative charge of the modified proteins or polypeptides and the antiviral activity. The more negative the active substance, the greater is the antiviral activity, in particular the anti-HIV activity.

In addition, the present inventions resides in a pharmaceutical preparation for treating viral infections and immunodeficiency diseases and for inhibiting fusion of virus infected cells with non infected cells, comprising: a reagent selected from a group consisting of reagents which prevent protonation of nitrogen containing basic groups and reagent which replace the nitrogen containing basic groups by one or more functional groups having a negative charge; and a modified polypeptide, wherein the modified polypeptide includes nitrogen containing basic groups, the modified polypeptide having an additional net negative charge resulting from the derivatisation of the said nitrogen containing basic groups by the reagent; wherein the modified polypeptide has a prolonged retention time of at least 9 minutes compared to a non derived polypeptide, the retention time being determined by a Fast Protein Liquid Chromatography System on an anion exchange column.

The present invention also resides in a process for treating illnesses, comprising the steps of: providing a pharmaceutical preparation comprising a reagent selected from a group consisting of reagents which prevent protonation of nitrogen containing basic groups and reagents which convert the nitrogen containing basic groups by one or more functional groups having a negative charge, a modified polypeptide, wherein the polypeptide includes nitrogen containing basic groups, the modified polypeptide having an additional net negative charge resulting from the derivatisation of the said nitrogen containing basic groups by the reagent, wherein the modified polypeptide has a prolonged retention time of at least 9 minutes compared to a non derived polypeptide, the retention time being determined by a Fast Protein Liquid chromatography System on an anion exchange column; and administering the preparation and treating the illnesses, wherein the illnesses are selected from the group consisting of viral infections and immunodeficiency diseases.

The present invention also resides in a process for inhibiting fusion of virus infected cells with non infected cells, comprising the steps of: providing a pharmaceutical preparation comprising a reagent selected from a group consisting of reagents which prevent protonation of nitrogen containing basic groups and reagents which convert the nitrogen containing basic groups by one or more functional groups having a negative charge, a modified polypeptide, wherein the polypeptide includes nitrogen containing basic groups, the modified polypeptide having an additional net negative charge resulting from the derivatization of the said nitrogen containing basic groups by the reagent, wherein the modified polypeptide has a prolonged retention time of at least 9 minutes compared to a non derived polypeptide, the retention time being determined by a Fast Protein Liquid Chromatography System on an anion exchange column; and administering the preparation to inhibit fusion of infected cells with non-infected cells, wherein the reagent for the preparation of the net negatively charged polypeptide is not maleic anhydride or succinic anhydride.

The present invention also resides in a method for preparing a pharmaceutical preparation, comprising the steps of: providing a modified polypeptide which contains nitrogen containing basic groups and a reagent which prevents protonation of nitrogen containing basic groups; combining the modified polypeptide and the reagent; deriving the nitrogen containing basic groups via the reagent and preventing protonation thereof and forming a modified polypeptide having an additional net negative charge and a prolonged retention time as compared to a polypeptide not derived; and determining the retention time via a Fast Protein Liquid Chromatography System on an anion exchange column, wherein the retention time is at least 9 minutes.

Still further, the present invention resides in a method for preparing a substance, comprising the steps of: providing polypeptides which contain nitrogen containing basic groups and a reagent which converts the nitrogen containing basic groups by one or more functional groups having a negative charge; combining the polypeptide and the reagent; deriving the nitrogen containing basic groups via the reagent, causing it to modify and acquire an additional net negative charge by replacing the nitrogen containing basic groups by the one or more functional groups having the negative charge, the step of deriving prolonging the retention time of the polypeptide as compared to a polypeptide not derived; and determining the retention time via a Fast Protein Liquid Chromatography System on an anion exchange column, wherein the retention time is at least 9 minutes.

The present invention also resides in a modified polypeptide, comprising a modified polypeptide including nitrogen containing basic groups, wherein the modified polypeptide has an additional net negative charge resulting from the derivatization of the nitrogen containing basic groups by a reagent, wherein the reagent is selected from a group consisting of reagents which prevent protonation of nitrogen containing basic groups and reagents which convert the nitrogen containing basic groups by one or more functional groups having a negative charge, wherein the modified polypeptide has a prolonged retention time of at least 9 minutes compared to a non derived polypeptide, the retention time being determined by a Fast Protein Liquid Chromatography System on an anion exchange column.

DETAILED DESCRIPTION OF THE PREFERRED EMBODIMENTS

As already stated above, the "additional net negative charge" can be quantified on the basis of the retention time. This retention time is determined, for example, in accordance with the following chromatographic method:

Prepare a solution of substance to be tested in a concentration of 1 mg/ml of a Tris.HCl buffer (0.02M) having a pH of 7.5 (buffer A).

Inject 100 $\mu$l of the sample into a FPLC system (Fast Protein Liquid Chromatography) from Pharmacia, Woerden, the Netherlands, which is provided with a mono-$Q^R$-hr 5/5 anion exchange column from Pharmacia.

Elute at a rate of 0.25 ml/min using a gradient of 100% buffer A to 100% buffer B, consisting of buffer A+1M NaCl, in 30 minutes.

Measure the retention time.

The retention time is the period (in minutes) in which an individual compound is retained on the defined protein separation column after application to that column, being a characteristic for total charge of the particular protein given the composition of the mobile phase.

The "additional net negative charge" can also be quantified in another way, that is to say on the basis of the theoretical net negative charge. This theoretical value is calculated by multiplying the number of derivatised groups by the change in charge per derivatised group, plus the charge of the starting material. In the case of the negatively charged polypeptides or modified proteins according to the invention, the net negative charge will be lower than −60 and, for example, of the order of magnitude of −60 to −300 and below.

The criterion of the theoretical net negative charge is illustrated with reference to the following examples.

In the compound Suc-HSA (a reaction product of human serum albumin and succinic anhydride) which can be used according to the invention, all 61 positive $NH_2$+of lysine have been replaced by negative $COO^-$ groups. Thus, there is a change in charge of 2 per lysine. The theoretical charge of this compound is therefore: −15 (from the original albumin or HSA)+(2x−61)=−137. For bovine serum albumin (BSA) the value for the Suc-BSA material would be−140 because the value of the charge on the original BSA is −18.

Suc-HSA, the reaction product of human serum albumin and succinic anhydride which can be used according to the invention, has a theoretical net negative charge of −137 (=−15+61 x −2).

Aco-HSA, the reaction product of human serum albumin and aconitic anhydride (anhydride of cis- or trans-prop-1-ene-1,2,3-tri-carboxylic acid) which can be used according to the invention, has a theoretical net negative charge of −198 (=−15+(61 x −3)).

The negative charge for the very stable reaction product of albumin and propane-1,2,3-tricarboxylic acid anhydride, which is to be preferred, is similar.

Moreover, the prolongation of the retention time compared with that of HSA, determined under the chromatography conditions described, is 13 minutes for Aco-HSA and 11.5 minutes for Suc.-HSA.

Moreover, the theoretical charge on the proteins/polypeptides is calculated as the average of the charge on all amino acids present in the molecule (about 600 amino acids in the case of serum albumin).

It is also possible to introduce three or more carboxyl groups per amino group/basic group into the starting materials which can be used according to the present invention. Of course, active materials are then obtained which have an even higher negative charge and a prolongation of the retention time which is even greater than the abovementioned value.

The modified proteins or polypeptides which contain an additional net negative charge and can be used in the pharmaceutical preparations according to the invention are designated "negatively charged polypeptides" in the remainder of this description. Compounds of this type are generally water-soluble and they can exist in ionic form.

The negatively charged polypeptides are preferably poly-amino acids and modified plasma proteins, such as albumin and α-acid glycoproteins ("orosomucoid"). Polypeptides having a molecular weight of the order of magnitude of about 70,000 are suitable. However, the molecular weight can also be appreciably higher or lower; the important factor is that a poly-anionic polypeptide structure is present in the molecule.

It has been found that lysine and histidine are preferred as groups to be derivatised in the negatively charged polypeptides to be used according to the invention. The nitrogen-containing group in lysine is an amino group, whereas the nitrogen-containing group in histidine is regarded as an "other basic functional group". Moreover, for example, polylysine can also be used successfully according to the invention.

Standard chemicals which are capable of introducing an additional net negative charge into the starting material are used to prepare the derivative. Preferably, however, aldehydes, anhydrides, acid chlorides and iso(thio)cyanates are used. It has been found that reagents of this type yield negatively charged polypeptides which provide a pharmaceutical preparation with an outstanding action against the abovementioned disorders and conditions.

The following substances may be mentioned as examples of reagents for preparing derivatives of proteins or polypeptides.

1. Anhydrides 1.1 Straight-chain anhydrides

Give, by reaction with amines in proteins, amide bonds which are not protonated at a physiological pH.

$NH_3^-$→neutral amide.

(change in charge of −1).

1.1.1 Symmetrical anhydrides:

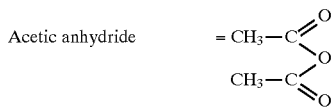

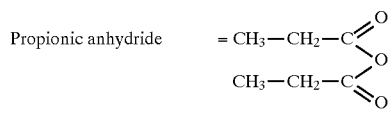

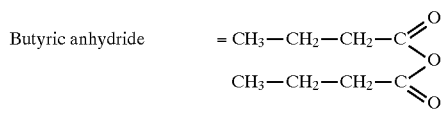

1.1.2. Asymmetric anhydrides:

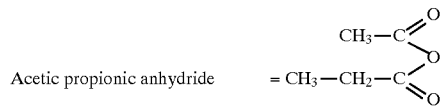

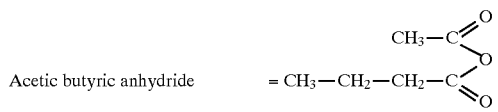

1.2.1. Cyclic anhydrides

Give, by reaction with amines in proteins, amide bonds which are not protonated at a physiological pH and in addition they introduce a carboxyl group which is deprotonated at a physiological pH.

$NH_3^-$→neutral amide+negative carboxyl group.

(change in charge of −2)

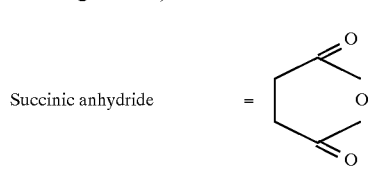

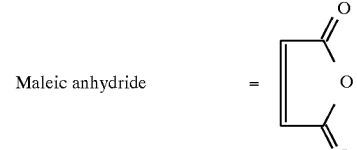

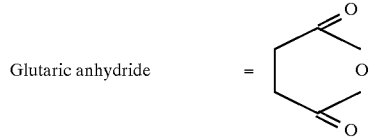

1.2.2. Cyclic anhydrides having an additional carboxyl group in the ring

Give, by reaction with amines in proteins, amide bonds which are not protonated at a physiological pH and in addition they introduce two carboxyl groups which are deprotonated at a physiological pH.

$NH_3^-$→neutral amide+2 negative carboxyl groups. (change in charge of −3).

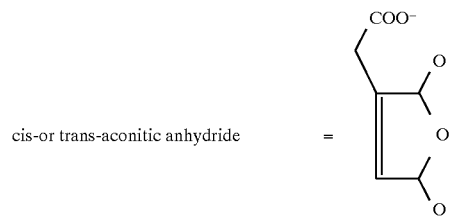

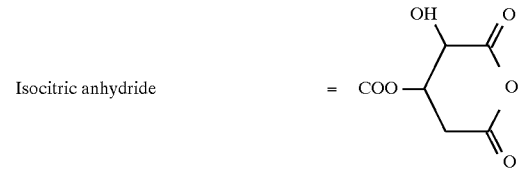

2. Acid halides (in general acid chlorides)

Give, by reaction with amines in proteins, amide bonds which are not protonated at a physiological pH.

$NH_3^-$→neutral amide.

(change in charge of −1).

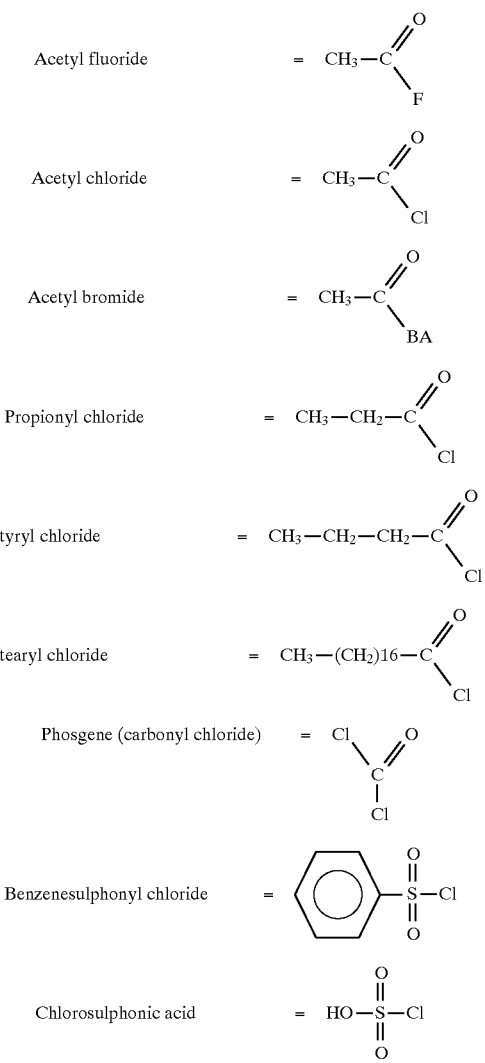

The last two give a change in charge of −2 because, in addition to the removal of the positive charge from the amino group, a negative charge is introduced on the sulphonyl group.

3. Aldehydes

Give imines by reaction with amines in proteins.
NH$_3^-$→neutral imine.
(change in charge of −1).

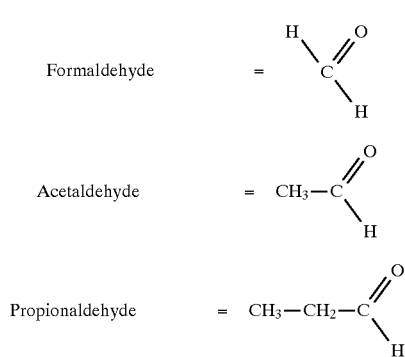

-continued

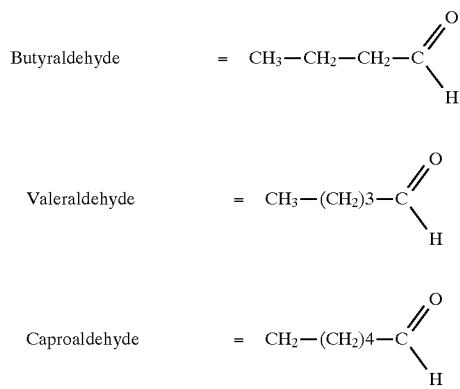

4. Isothiocyanates

Give, by reaction with amines in proteins, thiocarbamyl bonds which are not protonated at a physiological pH.

NH$_3^-$→neutral thiocarbamyl.
(change in charge of −1).

Fluorescein isothiocyanate =

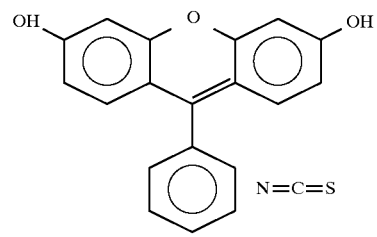

Rhodamine isothiocyanate =

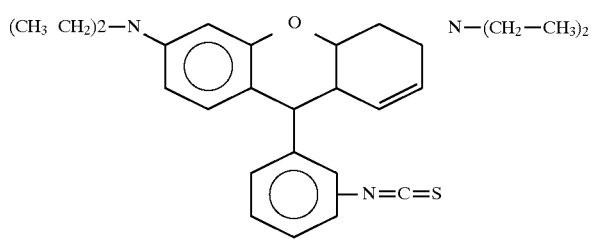

para-Isothiocyanatophenyl = 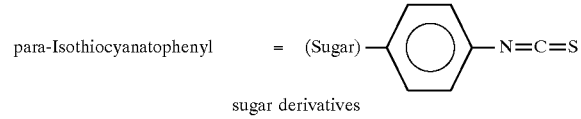
sugar derivatives

5. Isocyanates

Give, by reaction with amines in proteins, urea bonds which are not protonated at a physiological pH.

$NH_3^- \rightarrow$ neutral urea.

(change in charge of −1).

Benzene isocyanate = 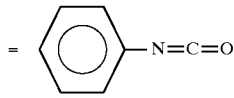—N=C=O

The abovementioned reagents for obtaining poly-anionic proteins or polypeptides are far from complete and give only a few examples from the various groups.

In the case of all reagents, additional anionic functional groups, such as phosphates, sulphates and carboxyl groups, can, where possible, be incorporated in the chain in such a way that additional negative charges are introduced.

Because the additional net negative charge on the polypeptides which are used according to the invention is very important for the action, the starting protein or starting polypeptide preferably contains as many groups as possible which can be derived and thus acquire an additional negative charge. Preferably, the natural or synthetic oligopeptides, which are used as starting materials, consist to the extent of more than 5%, in particular more than 15% and even more particularly more than 25% of amino acids which contain functional amino groups or other functional basic groups, for example the abovementioned lysine and histidine.

The preparations according to the invention can be administered enterally or parenterally. Preparations which can be administered parenterally or enterally can also be prepared from preparations according to the invention.

Medicinal preparations which contain the negatively charged polypeptides according to the invention can be in the form of powders, suspensions, solutions, sprays, emulsions, ointments or creams and can be used for topical application, for intranasal, rectal or vaginal administration, and also for oral or parenteral (intravenous, intradermal, intramuscular, intrathecal, and the like) administration. Such preparations can be prepared by combining the negatively charged polypeptides (for example by mixing, dissolving or the like) with pharmaceutically acceptable excipients of a neutral type, such as aqueous or non-aqueous solvents, stabilizers, emulsifiers, detergents and additives, and also, if desired, with colorants and aroma substances. The concentration of the negatively charged polypeptide in the preparation according to the invention can vary substantially and be between 0.001, preferably 0.1, and 100%, depending on the mode of administration. Furthermore, the dose of the negatively charged polypeptide to be administered can, for example, be between 0.1 mg and 100 mg/kg of body weight.

It is expected that by intravenous administration of aconiylated human serum albumin (Aco-HSA) either by infusion or by repeated single injection usually with a total input per day of at least 1.5 mg/kg body weight and maximally 15 mg/kg, long lasting antiviral concentrations will be attained in the blood stream and the lymphatic system of AIDS patients.

The invention also relates to the use of substances which have acquired an additional net negative charge, as defined above, as active substance or as substance contributing to the action, or as carrier for active substance when preparing pharmaceutical preparations which are suitable for treating or curing viral infections and immunodeficiency diseases such as retrovirus infections, including AIDS and AIDS-related diseases, and which can be used to inhibit fusion of infected with non-infected cells.

The invention also relates to a method for treating diseases or disorders caused by retrovirus infections such as AIDS and AIDS-related diseases, or conditions in which fusion of virus with cells or fusion of virus-infected cells with non-infected cells occurs, with which method an additionally negatively charged protein or polypeptide as defined above is used.

The invention also relates to a method for the preparation of modified proteins and polypeptides, with which method the amino groups and/or other basic functional groups of the proteins or polypeptides are derivatised with a reagent which prevents protonation of basic amino acids, the proteins or polypeptides acquiring an additional net negative charge such that the prolongation of the retention time of the protein or polypeptide derivative compared with that of the protein or polypeptide not converted to a derivative is at least 9 minutes, the retention time being determined by means of FPLC on an anion exchange column.

The invention also relates to the new modified proteins or polypeptides, comprising a protein or polypeptide in which the amino groups and/or other basic functional groups have been reacted with a reagent which prevents protonation of the basic amino acids and/or other basic groups or replaces said basic amino acids and/or other basic groups by one or more functional groups having a negative charge, such as chemical moieties of the modified polypeptide molecules, the modified protein or polypeptide having an additional net negative charge, compared with the non-modified protein or polypeptide, such that the prolongation of the retention time of the protein or polypeptide derivative, compared with that of the protein or polypeptide not converted to a derivative, is at least 9 minutes, the retention time being determined by means of FPLC on a column containing an anion exchanger.

According to the invention, it has been found that negatively charged polypeptides are, inter alia, powerful and selective anti-HIV agents which substantially reduce syncytium formation and virus-cell fusion, do not bind to the OKT4A epitope of the CD4 receptor and have only a slight inhibitory action on the interaction of anti-gp120 and mAb gp120 and the binding of virus cells at very low concentrations. The negatively charged polypeptides used or prepared according to the invention have no or only a low toxicity.

The invention is illustrated with reference to the investigation described below.

Investigation

Preparation of negatively charged albumin with the aid of formaldehyde and succinic anhydride (form-HSA and suc-HSA).

500 mg of HSA were dissolved in 50 ml of 0.2M $Na_2CO_3$ (pH 10.0), formaldehyde was added to give a final concentration of 20% by weight, based on the starting material, and the solution formed was stirred in the dark for 72 hours at room temperature. In order to remove insoluble material, the solution was filtered through a filter with 0.2 µm openings, purified on a Sephadex G25 column, washed with distilled water on a PM10 membrane in an Amicon "Stirred Cell Concentrator" and finally lyophilised, form-HSA being obtained.

500 mg of HSA were dissolved in 50 ml of 0.2M $K_2HPO_4$ (pH 8.0). 500 mg of solid succinic anhydride were added and the solution was stirred until the succinic anhydride had dissolved. The pH was kept between 8.0 and 8.5 using 6 M sodium hydroxide. Purification was carried out as described for form-HSA. Pure suc-HSA was obtained.

The additional net negative charge of the modified albumin was determined with the aid of a FPLC system (Fast Protein Liquid Chromatography) from Pharmacia, Woerden, the Netherlands, using a mono-Q anion exchange column from Pharmacia. Buffer A was a 0.02M Tris.HCl buffer (pH 7.4) and buffer B consisted of buffer A plus 1M NaCl. Elution was carried out at a rate of 0.25 ml/min, using a gradient of 100% A to 100% B in 30 minutes. The samples of the substance to be investigated were dissolved in an amount of 1 mg/ml in buffer A and in each case 100 µl were injected into the FPLC system.

MT-4 cells from a $T_4$ lymphocyte cell line carrying HTLV-I were used for the anti-HIV-1 test. The MT-4 cells were cultured in RPMI 1640 medium, supplemented with 10% by volume of heat-inactivated fetal calf serum (FCS) and 20 µg/ml of gentamicin. MOLT-4 cells (clone 8, cf. J. Virol. 57, 1159–1162) were used for the test relating to syncytium formation. The cells were kept in a moist atmosphere of 5% $CO_2$ in air at a temperature of 37° C. Every 3–4 days cells were centrifuged down and transferred to new culture flasks ($2\times10^5$ cells/ml). The cells were analyzed periodically for the presence of mycoplasma: they were always found to be free from mycoplasma.

HIV-1 (strain $HTLV-III_B$) was obtained from the culture fluid of HUT-78 cells infected with HIV-1. The virus titre of the culture fluid was determined in MT-4 cells. The virus was stored at −70° C.

The antiviral activity of the negatively charged polypeptides was determined on the basis of the inhibitory effect on virus-induced cytopathogenicity in MT-4 cells and was recorded with the aid of the 3-(4,5-dimethylthiazol-2-yl)-2,5-diphenyltetrazolium bromide (MTT) method, which is described in J. Virol. Methods 20, 309.321.

Syncytium formation was determined as follows. The modified polypeptides were diluted in RPMI and transferred to the wells of microtitre plates. $5\times10^4$ HIV-1-infected HUT-78 cells, which had previously been washed twice in order to remove free virus particles, were then added to the wells, immediately followed by the addition of $5\times10^4$ MOLT-4 cells, a final volume of 200 µl being obtained. The cell mixtures were cultured at 37° C. in a $CO_2$-containing cell incubator. The first syncytia were formed after 4–6 hours. After 24 hours the cells were analyzed by microscopic examination and laser flow cytofluorography.

The assay relating to virus adsorption was carried out as follows.

MT-4 cells were exposed to HIV-1 virions in the absence or the presence of the negatively charged polypeptides according to the invention. After incubation for 30 minutes at 37° C., the cells were washed in order to remove non-bound virus particles. The cells were then stained for indirect fluorescence using polyclonal antibody for HIV-1, and the HIV-1 particles bound to the cells were analyzed by laser flow cytofluorography.

The CD4 immunofluorescence assay was carried out using the method described in No. 42 Proc.Natl.Acad.Sci. USA 86, 3322–3326. MT-4 cells were incubated for various periods at room temperature in the absence and the presence of a negatively charged polypeptide. The cells were then stained with optimum concentrations of the mono-clonal antibodies OKT4A-FITC (orthodiagnostics) or anti-leu3a-PE and "Simultest immuno monitoring" with control material (FITC-labelled $IgG_1$ and PE-labelled $IgG_2$) (Becton Dickinson) for 20 minutes at 4° C., washed once in PBS and fixed in 0.5 ml of 0.5% by weight paraformaldehyde in PBS.

The investigations described above showed that a clear correlation exists between the antiviral activity and the negative charge. For example, by simple succinylation of the lysine groups of albumin an anionic compound is obtained which has a very low $IC_{50}$ (1 µg/ml). None of the negatively charged polypeptides tested was found to be cytotoxic at concentrations of up to 1000 µg/ml.

The Aco-HSA material was prepared analogously to the method described above. The anti-HIV activity of this material is very high: $IC_{50}$=0.0056 µg/ml. This compound is therefore 175 times more active than Suc-HSA and is one of the most active compounds known at present (approximately 25 times more active than AZT).

The negatively charged polypeptides according to the invention inhibit the virus adsorption to only a slight degree, for example in a concentration of 100 µg/ml. For comparison: dextran sulphate inhibited virus adsorption virtually completely at a concentration of 25 µg/ml.

The syncytium formation is appreciably reduced by the negatively charged polypeptides according to the invention, for example by 50% at a concentration of only about 2 µg/ml. In order to obtain a similar inhibition with, for example, dextran sulphate, a concentration of 28 µg/ml is needed, which amount is about 50 times higher than the $IC_{50}$ thereof in the antiviral assay (0.6 µg/ml).

It is known that OKT4A mAb binds to an epitope of the CD4 molecule, which is responsible for the HIV adsorption and can prevent binding of HIV particles to the cells. Aurintricarboxylic acid (ATA) gives specific interaction with this epitope of the CD4 molecule and was used as positive control. The OKT4A mAb-CD4 interaction was completely inhibited by ATA in a concentration of 25 µg/ml. The negatively charged polypeptides according to the invention (and also dextran sulphate) had no influence on this interaction in concentrations of up to 100 µg/ml, from which it can be concluded that the active substances according to the invention do not bind to this epitope of the CD4 receptor.

Persistently HIV-1-infected HUT-78 cells and a specific anti-gp120 mAb, which recognizes the V3 region of gp120 and which plays an important role in the formation of giant cells, were used in the investigation of the direct interaction of the negatively charged polypeptides with the viral gp120. Dextran sulphate inhibited the binding of anti-gp120 mAb to gp120 in a manner which is dependent on the concentration, the amounts involved being said to be equal to the amounts which have an antiviral action. The negatively charged polypeptides according to the invention also inhibit the anti-gp120-mAb-gp120 interaction in a manner which is dependent on the concentration. However, the concentration which is needed for a 50% inhibition is many times (for example 100 times) greater than the $IC_{50}$, from which it can be concluded that shielding of gp120 is probably not the only mechanism of action of the compounds according to the invention.

The mechanism of action of the compounds according to the invention is based on preventing the fusion of the virus with the cells and with a compound from the fusion of infected cells with non-infected cells. Very probably, the interaction of the compounds with viral fusion proteins (such as GP41 in the case of HIV) is essential here. This mechanism of action has never been described before.

Procedure for and results of further experiments relating to antiviral and anticoagulant action.

Reference is made to the appended Tables 1, 2, 3 and 4.

The antiviral activity of two substances according to the invention (Aco-HSA and Suc-HSA) against viruses causing immuno-deficiency is compared with the activity of dextran sulphate, another polyanionic antiviral compound. Conclusion: substances according to the invention are active against HIV-1, HIV-2, FIV and SIV.

The anti-HIV-1 test has already been described above.

HIV-2 ($LAV-2_{ROD}$) (obtained from Dr. L. Montagnier, Paris, France) was isolated from the medium supernatant of persistently $LAV-2_{ROD}$-infected MOLT-4 cells. The anti-HIV-2 test is identical to the anti-HIV-1 test.

FIV-48 and FIV-113 were isolated from peripheral mononuclear blood cells of seropositive wildcats. The anti-FIV test was carried out using the method of Egberink et al. (Proc.Natl.Acad.Sci. USA (1990) 87: 3087–3091).

Mitogen-stimulated cat thymocytes were plated out in 1.6 cm$^2$ wells ($10^6$ cells per ml) in the presence of various concentrations of the substances to be tested. After incubating for 1 hour at 37° C., FIV was added in an amount which corresponds to $6 \times 10^6$ cpm reverse transcriptase (RT) activity. After incubating for 1 hour at 37° C., the medium was replaced by fresh medium containing various concentrations of the substances to be tested. The RT activity in the supernatant was determined after incubating for 4 and 6 days at 37° C. (see Table 2).

The antiviral activity of two substances according to the invention (Aco-HSA and Suc-HSA) against DNA viruses is compared with the activity of dextran sulphate, another polyanionic antiviral compound. Conclusion: the substances according to the invention have no activity against the DNA viruses tested, in contrast to dextran sulphate.

Anti-CMV test: human embryonic lung (HEL) fibroblasts were cultured in MEM medium to which 10% fetal calf serum, 1% L-glutamine and 0.3% sodium bicarbonate were added. The cells were infected with 100 PFU (plaque forming units) of human cytomegalovirus (CMV, strain AD169 and Davis strain). At the same time, the substances to be tested were added in various concentrations. The virus plaque formation and the cell death caused by the virus were determined as described by Snoeck et al. (1988) 32, 1839–1844 (see Table 2).

The antiviral activity of two substances according to the invention (Aco-HSA and Suc-HSA) against RNA viruses is compared with the activity of dextran sulphate, another polyanionic antiviral compound. Conclusion: The substances according to the invention have no activity against the RNA viruses tested except for influenza. In contrast, dextran sulphate has an activity only against VSV and Sindbis virus.

The activity of the substances against polio virus, Coxsackie virus, VSV, Sindbis, Semliki Forest virus, reovirus, para-influenza virus, HSV-1, HSV-2 and VMW was determined in the following way:

Confluent cell cultures (Vero cells, HeLa cells and primary rabbit kidney cells) were inoculated with the various viruses to 100 times the $CCID_{50}$ (50% cell culture infective dose) in the presence of various concentrations of the substances to be tested. After 1 hour the medium was replaced by medium in which only the substances to be tested are still present in various concentrations. The cell death caused by the viruses was determined after 1 to 2 days post-infection for VSV; after 2 days for Coxsackie virus, Semlili Forest virus and polio virus; after 2 to 3 days for HSV-1, HSV-2 and Sindbis virus; and after 6 days for para-influenza virus and reovirus.

The activity of the substances to be tested against Sendai virus and influenza virus was determined by measuring the fusion of the viral membrane with erythrocyte ghosts and liposomes and with BHK-21 cells or $LLC-MK_2D$ cells. The $R_{15}$-dequenching method as described by Hoekstra et al. (1984), Biochemistry 23, 5675–5681 and Wildschut et al. in Molecular Mechanisms of Membrane Fusion, (S. Ohki, D. Doyle, T. D. Flanagan, S. W. Hui and E. Mayhew, editors) 1988, Plenum Press, New York, pp. 441–450 was used for this purpose.

To summarize: influenza virus and Sendai virus were labelled with $R_{15}$. This resulted in a 70% self-quenching of the fluorescence. 35 μl of a concentrated suspension of $R_{15}$-labelled virus were introduced into a cuvette containing liposomes and erythrocyte ghosts of various cells (in HEPES buffer) and the increase in fluorescence (dequenching) caused by the fusion was measured on-line (excitation 560 nm, emission 590 nm). The same procedure was carried out in the presence of various concentrations of the substances to be tested.

Other polyanionic antiviral compounds such as dextran sulphate and heparin have a serious anticoagulant activity as a significant negative side effect. The substances according to the invention do not have this side effect. Only Aco-HSA has a slight anticoagulant activity at high concentrations of, for example 100 μg/ml (that is more than 10,000×the antiviral concentration).

TABLE 1

Inhibitory effect ($IC_{50}$ μg/ml) of polyanionic compounds on retroviruses

|  | HIV-1 | HIV-2 | FIV | SIV |
|---|---|---|---|---|
| Suc-HSA | 0.9 | 78 | <0.1 | + |
| Aco-HSA | 0.025 | 5.9 | <0.01 | + |
| DS | 0.6 | 0.08 | ND | ND |

+ = activity determined
ND = not determined

TABLE 2

Inhibitory effect ($IC_{50}$ μg/ml) of polyanionic compounds on DNA viruses

|  | HSV-1 | HSV-2 | HSV field | VMW | CMV |
|---|---|---|---|---|---|
| Suc-HSA | >400 | >400 | ND | ND | >400 |
| Aco-HSA | >400 | >400 | >400 | >400 | >400 |
| DS | 0.7 | 1.0 | 2.0 | 2.0 | 0.2 |

TABLE 3

Inhibitory effect ($IC_{50}$ μg/ml) of polyanionic compounds on the replication of RNA viruses

| Virus | Aco-HSA | DS |
|---|---|---|
| Coxsackie | >400 | >400 |
| Polio | >400 | >400 |
| VSV | >400 | 7.0 |
| Sindbis | >400 | 2.0 |
| Semliki Forest | >400 | >400 |
| Reo-virus | >400 | >400 |
| para-influenza | >400 | >400 |
| influenza | 0.8 | >400 |
| Sendai | >400 | >400 |

TABLE 4

Anticoagulant action of the compounds, determined as APTT (sec)

| Conc. (μg/ml) | Dextran sulphate | Suc-HSA | Aco-HSA | Heparin |
|---|---|---|---|---|
| 100 | >400 | 37.7 | 51.1 | >400 |
| 50 |  |  | 42.0 |  |
| 30 |  |  | 37.8 |  |
| 20 |  |  | 35.1 |  |
| 10 | 69.4 | 33.0 | 33.0 | 220 |
| 5 | 49.0 | 37.2 | 36.2 | 140 |
| 3 | 43.6 | 35.8 | 35.9 | 65 |
| 1 | 37.4 | 36.2 | 37.0 | 40.5 |

TABLE 4-continued

Anticoagulant action of the compounds, determined as APTT (sec)

| Conc. (µg/ml) | Dextran sulphate | Suc-HSA | Aco-HSA | Heparin |
|---|---|---|---|---|
| 0.1 | 37.6 | 38.0 | 37.8 | 40.3 |
| 0.01 | 38.0 | 39.0 | 36.8 | 38.4 |

The compounds were dissolved in PBS of pH 7.2 and 30 µl were added to 270 µl of plasma.

As control, 30 µl of PBS were added to 270 µl of plasma, which resulted in an APTT value of 38.0 sec. APTT= activated partial thromboplastin time (seconds) APTT was determined electromechanically using standard methods.

In addition to the foregoing, there was performed ex vivo experiments on freshly prepared human blood lymphocytes and monocytes/macrophages infected with HIV-1 particles isolated from various AIDS patients (so-called clinical isolates). These studies demonstrated complete inhibition of viral replications with negatively charged polypeptides according to the present invention. The products proved to be fully active against syncytium inducing HIV variants isolated from AIDS patients in the fatal stage of the disease.

In addition, the lack of toxicity has been proven by in vivo animal studies. Further, in rats, mice and monkeys no toxicity and no immunogenicity at 50 mg/kg has been detected.

Extrapolation to human administration is allowed based on in vivo experiments in which it has been shown that the elimination of the products from the general circulation is relatively slow at concentrations 2–5 times the antiviral titers, due to saturation of the elimination process (endocytosis via scavenger receptors). Considering the well known similarities of human, monkey and rat scavenging systems for negatively charged proteins, it is anticipated that similar and acceptable kinetic patterns in humans can be expected. Based thereon, the residence time is definitely expected to be long enough for clinical efficacy.

The only reference compound for all in vitro activity experiments is AZT. Some of the modified proteins provide in vitro activities that are more than one order of magnitude higher, compared to AZT. Also, the dual active compounds of a negatively charged protein with e.g. AZT, according to the invention, exhibit high potency. The detected activities of these conjugates show a major synergistic effect on patient isolates of HIV.

The modified proteins of the present invention were tested in vivo in a HIV infection model in mice. Immunosuppressed mice can be grafted with human peripheral blood lymphocytes and challenged with HIV. Lp. administration of the compounds of the present invention resulted in a complete protection against virus injection. Repeated Lp. injection did produce sufficient blood levels and no evident toxicity was noticed.

The in vitro and in vivo data demonstrates a potent anti-HIV activity of the compounds of the present invention.

What is claimed is:

1. A pharmaceutical preparation which is suitable for treating viral infections other than HIV, which preparation contains a modified polypeptide, wherein said modified polypeptide comprises a polypeptide in which nitrogen containing basic groups have been reacted with a reagent which converts said nitrogen containing basic groups into functional groups which are not protonated at a physiological pH, wherein the modified polypeptide contains a polyanionic polypeptide structure and said functional groups are aconitate groups, wherein the modified polypeptide has an additional net negative charge compared to a non-modified polypeptide, and the modified polypeptide has a retention time prolonged by at least 9 minutes as compared to the non-modified polypeptide.

2. The preparation according to claim 1, wherein the nitrogen containing basic groups are basic amino groups.

3. The preparation according to claim 2, wherein the amino groups are selected from the group consisting of lysine residues, histidine residues and arginine residues.

4. The preparation according to claim 2, wherein the modified polypeptide contains amino acids amounting to at least about 5 wt % based on weight of the non-derived polypeptide.

5. The preparation according to claim 2, wherein the modified polypeptide is obtained from polyamino acids and modified plasma proteins.

6. The preparation according to claim 5, wherein the polyamino acids and modified plasma proteins are selected from the group consisting of albumins and glycoproteins.

7. The preparation according to claim 2, wherein the modified polypeptide comprises a modified protein.

8. The preparation according to claim 1, wherein the modified protein is serum albumin and the functional groups are aconitate groups.

9. The preparation according to claim 1, wherein the modified polypeptides which have acquired the net negative charge are present in an amount of 0.1–100 wt % based on the entire weight of the preparation.

10. The preparation according claim 1, wherein the functional groups are cis-aconitate groups.

11. The preparation according to claim 1, wherein the preparation further comprises an active substance for treating said viral infection, and wherein said modified polypeptide is a carrier for said active substance.

12. The preparation according to claim 1, wherein the viral infection is influenza.

13. A process for treating an illness other than HIV, comprising the steps of:
providing a pharmaceutical preparation which contains a modified polypeptide, wherein said modified polypeptide comprises a polypeptide in which nitrogen containing basic groups have been reacted with a reagent which converts said nitrogen containing basic groups into functional groups which are not protonated at a physiological pH, wherein the modified polypeptide contains a polyanionic polypeptide structure and said functional groups are aconitate groups, wherein the modified polypeptide has an additional net negative charge compared to a non-modified polypeptide, and the modified polypeptide has a retention time prolonged by at least 9 minutes as compared to the non-modified polypeptide; and
administering the preparation and treating the illness.

14. The process according to claim 13, wherein the illness is selected from the group consisting of viral infections and immunodeficiency diseases.

15. The process according to claim 13, wherein the functional groups are aconitate groups.

16. The process according to claim 13, wherein the step of providing the preparation further comprises providing an active substance for treating said illness, and using said modified polypeptide as a carrier for said active substance.

17. The process according to claim 13, wherein the preparation is administered as an anti-virally active substance.

18. A method according to claim 13, wherein the functional groups are cis-aconitate groups.

19. A process for in-vitro inhibition of fusion of virus infected cells with non-infected cells, comprising the steps of:

providing a pharmaceutical preparation which contains a modified polypeptide, wherein said modified polypeptide comprises a polypeptide in which nitrogen containing basic groups have been reacted with a reagent which converts said nitrogen containing basic groups into functional groups which are not protonated at a physiological pH, wherein the modified polypeptide contains a polyanionic polypeptide structure and said functional groups are aconitate groups, wherein the modified polypeptide has an additional net negative charge compared to a non-modified polypeptide, and the modified polypeptide has a retention time prolonged by at least 9 minutes as compared to the non-modified polypeptide; and administering the preparation to inhibit fusion of infected cells with non-infected cells.

20. The process according to claim 19, further comprising the steps of providing an active substance for inhibiting fusion, and using said preparation as a carrier for said active substance, whereby said administering step administers said preparation and said active substance.

21. A method according to claim 19, wherein the functional groups are cis-aconitate groups.

22. A modified polypeptide, comprising a polypeptide in which nitrogen containing basic groups have been reacted with a reagent which converts said nitrogen containing basic groups into functional groups which are not protonated at a physiological pH, wherein the modified polypeptide contains a polyanionic polypeptide structure and said functional groups are aconitate groups, wherein the modified polypeptide has an additional net negative charge compared to a non-modified polypeptide, and the modified polypeptide has a retention time prolonged by at least 9 minutes as compared to the non-modified polypeptide.

23. The modified polypeptide according to claim 22, wherein said modified polypeptide is a carrier for an active substance.

24. The polypeptide according to claim 22, wherein the nitrogen containing basic group is an amino group.

25. The polypeptide according to claim 22, wherein the polypeptide comprises a protein.

26. A modified polypeptide according to claim 22, wherein the functional groups are cis-aconitate groups.

27. A method for preparation of a modified polypeptide, comprising the steps of:

providing a polypeptide having nitrogen containing basic groups; and derivatizing the polypeptide with a reagent which converts said nitrogen containing basic groups into functional groups which are not protonated at a physiological pH so as to provide said modified polypeptide having a polyanionic polypeptide structure, whereby the modified polypeptide acquires an additional net negative charge compared to a non-modified polypeptide, and the modified polypeptide has a retention time prolonged by at least 9 minutes as compared to the non-modified polypeptide, wherein the reagent is aconitic acid.

28. The method according to claim 27, wherein the reagent is cis-aconitate anhydride.

29. The method according to claim 27, wherein the functional groups are aconitate groups.

30. The method according to claim 27, wherein the nitrogen containing basic group is a basic amino group.

31. The method according to claim 27, wherein the polypeptide comprises a protein.

32. The method according to claim 27, further comprising the step of providing an active substance for treating viral infections and immunodeficiency diseases and for inhibiting fusion of virus infected cells with non-infected cells, and using said modified polypeptide as a carrier for said active substance.

* * * * *